United States Patent
Simond et al.

(10) Patent No.: US 7,233,823 B2
(45) Date of Patent: Jun. 19, 2007

(54) APPARATUS FOR MEASURING BODY COMPOSITION

(75) Inventors: Bénédicte Simond, Bloye (FR); Alain Duborper, Sales (FR); Michel Sarrazin, Massingy (FR)

(73) Assignee: SEB S.A., Ecully (FR)

( * ) Notice: Subject to any disclaimer, the term of this patent is extended or adjusted under 35 U.S.C. 154(b) by 387 days.

(21) Appl. No.: 10/467,629

(22) PCT Filed: Oct. 11, 2002

(86) PCT No.: PCT/FR02/03477

§ 371 (c)(1),
(2), (4) Date: Aug. 8, 2003

(87) PCT Pub. No.: WO03/030735

PCT Pub. Date: Apr. 17, 2003

(65) Prior Publication Data

US 2004/0077968 A1   Apr. 22, 2004

(30) Foreign Application Priority Data

Oct. 12, 2001   (FR) .................................. 01 13193

(51) Int. Cl.
*A61B 5/05* (2006.01)

(52) U.S. Cl. ..................................... 600/547

(58) Field of Classification Search ................. 600/547, 600/548, 372, 382, 587, 595, 535
See application file for complete search history.

(56) References Cited

U.S. PATENT DOCUMENTS

| | | | | |
|---|---|---|---|---|
| 5,086,781 | A | * | 2/1992 | Bookspan .................... 600/547 |
| 5,579,782 | A | * | 12/1996 | Masuo ....................... 600/547 |
| 6,058,325 | A | | 5/2000 | Baura |
| 6,208,890 | B1 | | 3/2001 | Sarrazin et al. |
| 6,377,845 | B1 | * | 4/2002 | Kinast ........................ 600/547 |

FOREIGN PATENT DOCUMENTS

| | | |
|---|---|---|
| EP | 0 940 120 | 9/1999 |
| EP | 1 080 686 B1 | 3/2004 |
| FR | 2 698 779 A1 | 6/1994 |
| WO | PCT/KR95/00119 | 3/1996 |
| WO | WO 98/37829 A1 | 9/1998 |

* cited by examiner

*Primary Examiner*—Max F. Hindenburg
*Assistant Examiner*—Fangemonique Smith
(74) *Attorney, Agent, or Firm*—Browdy and Neimark, PLLC

(57) ABSTRACT

The invention concerns an apparatus for measuring a subject's body composition comprising a first electronic module (6) for measuring a bioelectric impedance and at least an electric power source (10) for generating a variable electric signal (11) which passes through the body or part of the body of the subject when the latter is connected to the measuring apparatus (2). The invention is characterized in that said power source is a voltage generator (10) designed to supply a rectangular voltage signal (11).

14 Claims, 2 Drawing Sheets

APPARATUS FOR MEASURING BODY COMPOSITION

The present invention concerns an apparatus for measuring body composition having an electrical measuring circuit associated with a unit for calculating the bioelectric impedance of a person.

Measurement of the body composition gives indications of the state of health of a person. More particularly, knowledge of the quantity of fat of the organism and of its evolution over time, constitutes an effective aid during a diet. Among the methods for measuring body fat, one notes measurement of the impedance of the human body correlated with the quantity of water in the body; the human body is composed of lean mass, constituted by muscles, bone, organs and tissues, of fatty mass. Water constitutes around 70% of the lean mass, while the fatty mass hardly contains any. Consequently, by measuring the electrical impedance of the human body and the total weight of a person, one can calculate, with some adjustment parameters, the fatty mass and the lean mass of the person.

Measurement of the bioelectric impedance is based on the conductivity of the tissues during passage of a brief alternating current of high frequency and low intensity. Dr. Boulier-Paris University V-Paris-France originated a concept utilizing the single measurement of a body segment (torso or lower members) traversed by an electrical signal of very high frequency (greater then 100 kHz) in order to establish the overall body composition thus permitting in this way the utilization of a weighing scale as a measuring support. He established the first scientific validation of this concept in 1994 (Doctoral Thesis of Human Biology-Rene Descartes University-Paris V. 1994 p 85-86).

Such a measurement apparatus is described in the document FR-A-2698779 where the value or the impedance of the body is obtained by utilizing the association of a weighing scale platform and of a plate furnished with four electrodes, two of which are associated with a circuit having a current generator and the two others are connected to a measuring apparatus. Thus, one calculates the value of the impedance of the body part measured as a function of the measured voltage, while knowing the constant current applied, and then one calculates the lean mass and the fatty mass by applying adjustment factors as a function, inter alia, of the size, of the age and by integrating the weight of the person. This apparatus is easy to use, but the measurements are not completely reliable, these latter being able to be falsified for example in the case of persons having edema or water retention problems.

In studying the electrical behavior of the human body, one notes that it can be assimilated to a suspension of cells in a conductive and homogeneous electrolytic solution. The intracellular an extracellular conductive media separated by a lipoproteic membrane constituting the cellular membrane. The Fricke model assimilates the electric behavior of the human body to an electric circuit composed of a capacitance C representing the cellular membrane connected in series with an intracellular resistance $R_i$ representing the electric resistance of the intracellular medium, the two being connected in parallel with the extracellular resistance $R_e$. In order to associate in a reliable manner the impedance measurements effectuated in the presence and the localization of the water in the organism, notably in the intracellular medium and in the extracellular medium, it is necessary to know their respective resistances $R_i$ and $R_e$.

A solution has been proposed in the document FR-A-2775581 in the name of the applicant. This document describes an apparatus for measuring the body composition using a current source that applies a current signal in square wave form and of an adjustable duration between the excitation electrodes of the apparatus. Voltage measurement are then effected between the measurement electrodes to determine the overall impedance of the measured body part and the extracellular resistance and in order to deduce therefrom as a result the intracellular resistance. Operating satisfactorily, this apparatus is found to be of a construction that is delicate and costly. Thus, the calculation method utilized demands that the measurement be effectuated at extremely precise moments and, at the same time, that the current signals applied be very precise and that they have a perfectly balanced duty cycle. Now, the utilization of such a current generator requires the use of transistors that are very sensitive to the operating conditions of the apparatus, for example, to temperature variations, which is translated on the signal by a generated current value that is influenced by the ambient temperature.

The goal of the present invention is to overcome the above-cited drawbacks and to propose an apparatus for measuring body composition that is able to effectuate precise measurements, without being influenced by ambient conditions during its operation.

Another goal of the invention is an apparatus for measuring body composition that is easy to place into use, while operating reliably.

A supplementary goal of the invention is an apparatus for measuring body composition that is of a simplified construction, that can be mass produced at a minimum cost.

These goals are achieved with an apparatus for measuring the body composition of an individual having a first electronic module intended to measure a bioelectric impedance and at least one electrical energy source intended to generate a variable electrical signal that passes through the body or a part of the body of the individual when this latter is connected to the measuring apparatus, by the fact that said energy source is a voltage generator intended to furnish a voltage signal of rectangular waveform.

Thus, the utilization of a voltage generator as the energy source presents the advantage of being able to continuously furnish a constant signal, having a value equal to or lower than that of the supply voltage. For example, the apparatus can make use of a microprocessor that directly generates a voltage equal to its supply voltage, with an electronic voltage regulator that permits maintenance of the supply voltage of the totality of the electronic arrangement constant regardless of the voltage level of the batteries of the apparatus. By this fact, and by its internal architecture, the microprocessor alone is capable of generating a square wave voltage signal, of which the voltage thresholds have values as precise as the precision of the voltage regulator. This microprocessor can advantageously be the same as that utilized to perform calculations permitting the termination of the extracellular and intracellular resistance of the organism, as will be explained below.

Such was not the case with a current generator according to the document FRA-2775581 of the prior art where the various components utilized being sensitive to ambient parameters, the apparatus required the introduction into the electronic assembly of a temperature compensation system that was costly and difficult to adjust with precision.

Now, in the apparatus of the invention, the electric signal that passes through the body of the individual is produced by a voltage generator, generator that thus furnishes a stable signal, of good quality for a minimum cost and a greatly facilitated implementation.

Moreover, the fact of using, on the one hand, a signal of rectangular waveform and, on the other hand, a voltage permits the avoidance of a complex and less precise phase shift measurement, as in the case of the apparatus for measuring bioelectric impedance according to the prior art that utilizes a sinusoidal signal and a multi-frequency treatment and, simultaneously, permits separation from the capacitive effect of the body tissues and measurement of the intracellular and extracellular resistances in a simpler manner, without relying on measurements at extremely precise moments and without utilizing signals having a perfectly balanced duty cycle, as in the case of the above-mentioned patent in the name of the applicant. With a voltage signal one thus arrives at measuring the intracellular and extracellular resistances in a simplified manner, starting from a single and unvarying signal in the course of the same measurement.

Advantageously, the apparatus of the invention comprises means permitting voltage measurement to be effectuated at at least two predetermined moments of the duration of said signal in order to directly determine the equivalent resistance $R_{eq}$ of the body or of the measured part of the body of the individual at these two moments and to deduce therefrom its extracellular resistance $R_e$ and it intracellular resistance $R_i$.

Thus, with only two measurements one can deduce from the equivalent resistance $R_{eq}$ at these two moments, by effectuating the necessary calculations, the values of the intracellular and extracellular resistances, values that are essential in the calculation of the body composition of the individual, notably in the determination of the distribution of water in the tissues.

Preferably, the apparatus of the invention comprises means permitting a first voltage measurement to be effectuated, at the end of a plateau of said signal of rectangular waveform, to determine the equivalent resistance $R_{eq}$, equal to the extracellular resistance $R_e$, as well as a second voltage measurement, at the end of a rising edge of said signal to determine the equivalent resistance $R_{eq}$ equal to $R_e$ in parallel with $R_i$, and to determine, on the basis of the first measurement, the intracellular resistance $R_i$ of the body or of the measured part of the body of the individual.

A plateau of said signal can be considered in theory as a constant signal and in practice a very low frequency (lower than 10 kHz) while a transition edge, rising or falling, of said signal can be considered in theory as a signal of infinite frequency and in fact is greater than 100 kHz. Thus, by effectuating a measurement at the end of a plateau of said signal, the membrane capacitance C of the measured part of the body of the individual is considered as an open circuit, while at the end of a rising edge, the membrane capacitance C is like a short circuit, which permits a determination of the values of said resistances without taking into account the values of the membrane capacitance C.

Preferably, said voltage generator is intended to furnish a voltage signal that presents a wave form whose period, amplitude and duty cycle are adjustable.

Adjustment of the period and of the duty cycle of said signal permit the best measurement of the extra cellular resistance of the body or of the measured part of the body by adapting the duration of a plateau of the signal at the end of which one effectuates the measurement in order to achieve a complete charging of the membrane capacitor C in order to be able to consider it as a open circuit.

Usefully, said voltage generator is intended to furnish a voltage signal that is a low voltage signal with an amplitude comprised between 3 and 6V. The electric current supplied is not greater that 800 μA.

Such a voltage protects the individual during utilization of the apparatus, while assuring a signal that is sufficiently large to effectuate precise measurements.

Preferably, the apparatus of the invention has a second electronic module intended to measure the weight of the individual.

Thus, the second module can measure the weight of the individual which is directly furnished to the apparatus, which avoids having to manually enter the weight data in order calculate his or her body composition.

Usefully, the first electronic module and the second electronic module are connected to a calculation unit able to determine the body composition of the individual. This calculation unit can advantageously be a microprocessor.

The data obtained during the measurements effectuated with the two electronic modules of the apparatus are transmitted to a calculation unit, notably a microprocessor that stores in memory the calculation equations and that then produces the information on the body composition of the individual.

Advantageously, the invention has a display means for the measured values and the calculated values.

Thus, the user of the apparatus can be informed at any moment and in real time of the values measured and/or calculated by the apparatus.

Preferably, the apparatus according to the invention has at least two excitation electrodes intended to apply said electric signal between a first point and a second point on the body of the individual and at least two measurement electrodes at the terminals of which a voltage is measured.

One can in principle achieve a bioelectric impedance measurement by utilizing only two electrodes applied to the body of the individual and connected to the measurement circuit. However, the use of four electrodes, two of which are for application of the signal and two for measurement, permits to pass as well the cutaneous barrier at the point of contact of the body of the individual with the electrodes and to thus effectuate measurements directly at the terminals of the electric circuit representing the measured part of the body of the individual.

The characteristics of the invention can advantageously be found in a weighing scale having a first electronic module intended to measure a bioelectric impedance and at least one source of electrical energy intended to deliver a variable electric signal that passes through the body or a part of the body of the individual when this latter is connected to a measuring apparatus, by the fact that said energy source is a voltage generator intended to furnish a voltage signal having a rectangular waveform.

The invention concerns equally a process for measuring the bioelectric impedance of the body or of a part of the body of an individual, where a rectangular voltage signal is applied between two excitation electrodes connected to the individual, the voltage between two measurement electrodes equally connected to the individual is measured at at least two predetermined moments of the duration of said rectangular signal permitting a direct determination of the equivalent resistance $R_e$, at these two moments of the body or of the measured part of the body of the individual traversed by the electrical signal and to deduce therefrom its extracellular resistance $R_e$ and its intracellular resistance $R_i$ and the body composition of the individual is determined by utilizing the measured values and a calculation unit.

Preferably, according to the process of the invention, a first voltage measurement is effectuated at the end of a plateau of said signal of rectangular waveform, in order to determine the equivalent resistance $R_{eq}$ equal to the extracellular resistance $R_e$, as well as a second voltage measurement, at the end of a rising edge of said signal to determine the equivalent resistance $R_{eq}$ equal to $R_e$ in parallel with $R_i$ and to determine, on the basis of the first measurement, the intracellular resistance $R_i$ of the body or of the measured part of the body of the individual.

Other characteristics and advantages of the invention will appear more clearly in light of the description and the drawings that follow, illustrating, by way of nonlimiting examples, embodiments of the invention.

Thus, reference is made to FIGS. 1 to 6, where:

Figure 3:
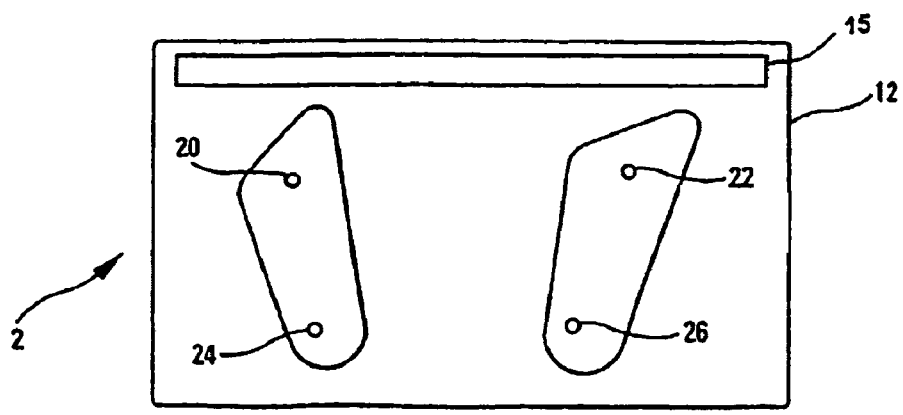
FIG. 3 represents a top plan view of the apparatus of the invention.

The apparatus for measuring the body composition 2 of an individual, human or animal, according to the invention is presented, as shown in FIG. 3, in the form of a plate 12 provided with four electrodes, two of which are for excitation or application of the signal 20, 22 between two points of the body of the individual, and two other measurement electrodes 24, 26. The electrodes can be arranged in a manner to come in contact with the feet of the individual when he or she is standing on horizontal plate 12 in order for a measurement to be taken. Electrodes 20, 22, 24, 26 are made of stainless steel or any other electrically conductive material, while plate 12 is made of an insulating material, for example a plastic material. One can equally dispose on plate 12 a display device 15 for the values measured and/or calculated by apparatus 2.

Advantageously, plate 12 is associated with a load applying plate of a weighing scale, in which case the information read by this latter is transmitted directly to the electronic circuit of the apparatus.

Figure 1:
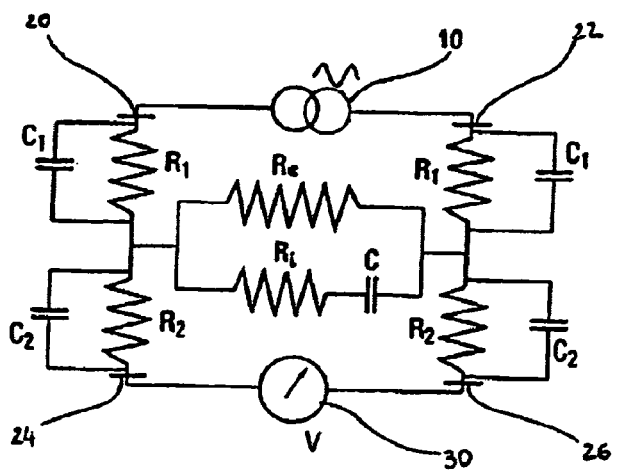
FIG. 1 represents a diagram of the principle of measurement of the bioelectric impedance utilizing four electrodes, according to the prior art.
Figure 2:
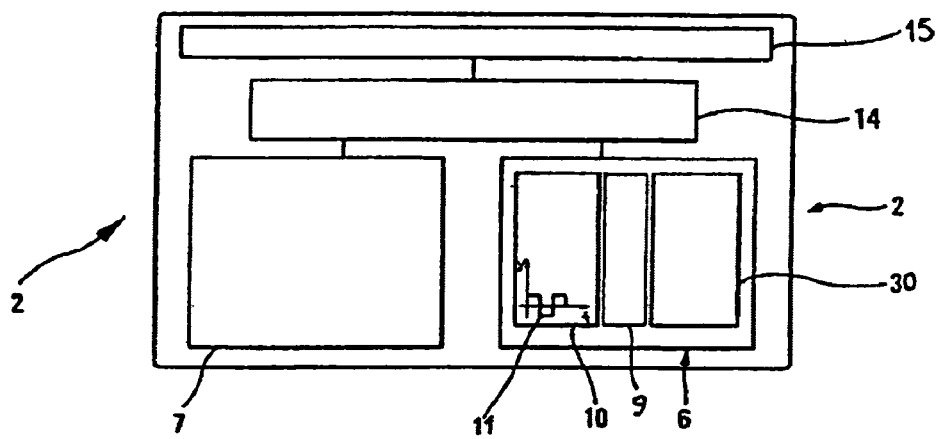
FIG. 2 represents a block diagram of an apparatus for measuring the body composition according to the invention.

As is visible in FIG. 2, the electronic circuit of apparatus 2 of the invention has a first electronic module 6 intended to measure the bioelectric impedance of an individual. This module is constituted by an electric energy source, notably a voltage generator 10, permitting the sending of an electric signal 11 passing through the body or a part of the body of the individual when this latter is connected to the electrodes of the apparatus, by a measurement unit 30 and by a signal treating unit 9. Measurement unit 30 recovers electric signal 11 after its passage into the body of the individual between measurement electrodes 24, 26.

The apparatus of the invention has a second electronic module 7 intended to measure the weight of the individual. First electronic module 6 and second electronic module 7 are connected to a calculation unit 14, notably a microprocessor or a microcontroller adapted to the treatment to be preformed. Calculation unit 14 is connected to display device 15 for the values measured and/or the values calculated by apparatus 2.

Figure 4:
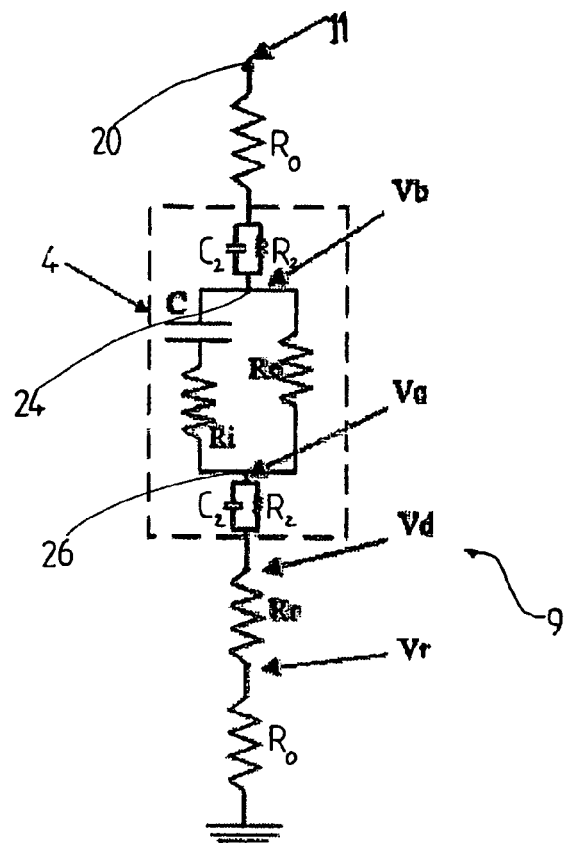
FIG. 4 represents a circuit diagram for the measurement of the parameters of the body composition while utilizing the apparatus of the invention.

FIG. 4 illustrates the circuit diagram of signal treating unit 9 according to the invention of first electronic module 6 of apparatus 2. On the diagram there is found the electric signal 11 applied to excitation electrode 20. The reference 4 designates an electrical model of the body or of the measured part of the body of the individual, notably of the human body, according to the Fricke model, where $R_i$ and $R_e$ are intracellular and extracellular resistances and C represents the membrane capacitance of the human body or of the measured part of the human body. References 24 and 26 designate the measuring electrodes and $R_2$ and $C_2$ are the resistances and the capacitances of cutaneous contact of the part of the body connected to the electrodes, notably the feet. $R_O$ represents a connection resistance.

With the diagram of FIG. 4 it is proposed to measure the voltages $V_b$ and $V_c$ on each of the measurement electrodes 24, 26 of the apparatus, as well as the voltages $V_d$ and $V_r$ at the terminals of a calibrated reference resistance $R_r$, having a good precision.

Thus, by measuring the voltages $V_d$ and $V_r$ one obtains the potential difference:

$$V_d - V_r = R_r \cdot i$$

from which one can deduce the intensity of the electric current represented:

$$i = (V_d - V_r)/R_r$$

In the same manner, by measuring the voltages $V_b$ and $V_c$ one obtains the potential difference:

$$V_b - V_c = R_{eq} \cdot i$$

By replacing in this formula i calculated previously, one obtains:

$$R_{eq} = (V_b - V_c)/i = R_r \cdot (V_b - V_c)/(V_d - V_r) \quad (1)$$

where, in this relation $R_{eq}$ represents the equivalent resistance of the lower members of the body of the individual at the moments of measurement of voltages $V_b$, $V_c$, $V_d$ and $V_r$.

Figure 5:
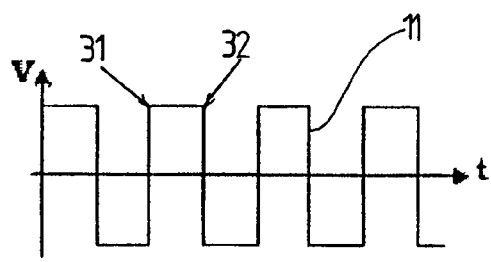
FIG. 5 represents the waveform of the electric signal generated according to a first embodiment of the invention.

The signal utilized has a voltage with a rectangular or square waveform of which the duration, the amplitude and the duty cycle are adjustable. FIGS. 5 shows the electric signal 11 utilized in the measurement of the body composition according to a first embodiment of the invention.

The particularity of electric signal 11 generated is to present at the point 31, at a rising edge, a signal of infinite frequency and at the point 32, at the end of a plateau, a signal of very of low frequency. It is known moreover that the membrane capacitance C of the circuit shown behaves like a short-circuit at high frequency, while at low frequency it behaves like an open circuit.

Thus, measurement of four voltages $V_b$, $V_c$, $V_d$, and $V_r$ are effectuated at moments 31 and 32, which permits to deduce:

At point 31: $1/R_{eq} = 1/R_e + 1/R_i$, with C in short-circuit, $R_e$ and $R_i$ in parallel, from which $$R_{eq} = (R_e \cdot R_i)/(Re + Ri) \quad (2)$$

at point 32: $R_{eq} = R_e$, with C open-circuited.

Consequently, a measurement of the voltages $V_b$, $V_c$, $V_d$ and $V_r$ at the point 32 permits to deduce with the relation (1) the value of $R_e$:

$$R_e = R_{eq} = R_r \cdot (V_b - V_c)/(V_d - V_r) \quad (3)$$

A second measurements of the voltages $V_b$, $V_c$, $V_d$, and $V_r$ at point 31 permits to deduce with relation (2) the value of the $R_i$:

$$R_i = R_e \cdot R_{eq}/(R_e - R_{eq})$$

where $R_{eq}$ is calculated with the relation (1) by introducing the voltage values measured at point 31 and the value of the $R_e$ has been determined at point 32 with the relation (3).

In conclusion, with the same signal one can determine $R_{eq}$ as well as the intracellular resistance $R_i$ and the extracellular resistance $R_e$. The values $R_i$ and $R_e$ are essential for calculating the fatty mass and the lean mass. The calculations are effectuated by calculation unit 14 on the basis of mathematical formulas stored in its memory. These formulas incorporate other parameters such as: weight, size, age, etc. Thus, a precise measurement of the total resistance represented by $R_i$ in parallel with $R_e$ permits a determination of the quantity of fatty mass and of lean mass, and the precise measurements of $R_i$ and $R_e$ permit an observation of the distribution of water and detection, for example the presence of an edema, or water retention problems, or also these measurements permit a determination of the quantity of fatty mass and of lean mass in infants who present an abrupt variation over time in the quantity of water contained in the muscle tissues.

Figure 6:
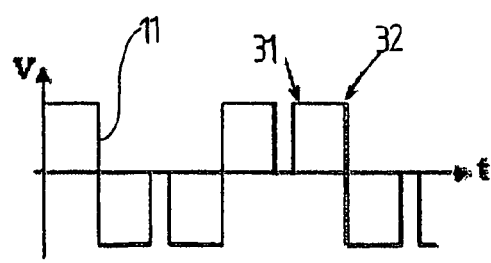
FIG. 6 represents the waveform of the electric signal generated according to a second embodiment of the invention.

FIG. 6 shows a second embodiment of the invention having an electric voltage signal 11 having a rectangular or square wave form where signal 11 is suppressed at the middle of each half cycle. Thus, resistances $R_i$ and $R_e$ are calculated by effectuating voltage measurements at the points 31, 32 as previously described. This embodiment permits avoidance of progressive charging of the capacitances representing the membrane walls.

First electronic module 6, the signal treating unit, measurement unit 30 together with calculation unit 14 and display device 15 can constitute an independent apparatus for measuring body composition or they can be integrated into other apparatus for example a weighting scale, or an apparatus for massaging, fitness, etc.

Other variants and embodiments of the invention can be envisioned without departing from the framework of its claims.

The invention claimed is:

1. Apparatus for measuring the body composition of an individual having a first electronic module (6) for measuring a bioelectric impedance and at least one electrical energy source intended to generate a variable electrical signal that passes through the body or a part of the body of the individual when the body or the part of the body of the individual is connected to said at least one electrical energy source, characterized in that said at least one energy source is a voltage generator (10) adapted to apply a voltage signal (11) of rectangular waveform across the body or the part of the body of the individual, and said module comprises means for obtaining voltage measurements across the body or the part of the body of the individual based on the voltage signal of rectangular waveform and for determining, on the basis of the voltage measurements, at least one of: the extracellular resistance $R_e$ of the body or of the part of the body of the individual; the intracellular resistance $R_i$ of the body or of the part of the body of the individual; and a value that is a combination of the extracellular resistance and the intracellular resistance of the body or of the part of the body of the individual.

2. Apparatus according to claim 1, characterized in that said apparatus comprises means permitting voltage measurement to be effectuated at at least two different predetermined moments in order to directly determine the equivalent resistance $R_{eq}$ of the body or of the part of the body of the individual at two of the moments and to deduce therefrom the extracellular resistance $R_e$ and the intracellular resistance $R_i$ of the body or of the part of the body.

3. Apparatus according to claim 1, characterized in that said apparatus comprises means permitting a first voltage measurement to be effectuated, at the end of a plateau (32) of said voltage signal (11) of rectangular waveform, to determine the equivalent resistance $R_{eq}$ equal to the extracellular resistance $R_e$ of the body or of the part of the body, as well as a second voltage measurement, at the end of a rising edge (31) of said signal (11) to determine the equivalent resistance $R_{eq}$ equal to $R_e$ in parallel with $R_i$, and to determine, on the basis of the first voltage measurement, the intracellular resistance $R_i$ of the body or of the part of the body of the individual.

4. Apparatus according to claim 1, characterized in that said voltage generator (10) is intended to furnish a voltage signal (11) that presents a wave form whose period, amplitude and duty cycle are adjustable.

5. Apparatus according to claim 1, characterized in that said voltage generator (10) is adapted to furnish a voltage signal (11) that is a low voltage signal with an amplitude comprised between 3 and 6V.

6. Apparatus according to claim 1, characterized in that said apparatus has a second electronic module (7) adapted to measure the weight of the individual.

7. Apparatus according to claim 6, characterized in that the first electronic module (6) and the second electronic module (7) are connected to a calculation unit (14) comprising said means for obtaining voltage measurements and able to determine the body composition of the individual.

8. Apparatus according to claim 7, characterized in that the calculation unit (14) is a microprocessor.

9. Apparatus according to claim 1, characterized in that said apparatus has a display means (15) for the measured values and the determined values.

10. Apparatus according to claim 1, characterized in that said apparatus has at least two excitation electrodes (20, 22) intended to apply said voltage signal (11) between a first point and a second point on the body of the individual and at least two measurement electrodes (24, 26) having terminals between which a voltage is measured.

11. Weighing scale having a first electronic module (6) for measuring a bioelectric impedance of an individual and at least one source of electrical energy intended to deliver a variable electric signal that passes through the body or a part of the body of the individual when the body or the part of the body is connected to a measuring apparatus (2), characterized in that said at least one energy source is a voltage generator (10) adapted to apply a voltage signal (11) having a rectangular waveform across the body or the part of the body of the individual, and said weighing scale comprises means for obtaining voltage measurements across the body or the part of the body of the individual based on the voltage signal of rectangular waveform and for determining, on the basis of the voltage measurements, at least one of: the extracellular resistance $R_e$ of the body or of the part of the body of the individual; the intracellular resistance $R_i$ of the body or of the part of the body of the individual; and a value that is a combination of the extracellular resistance and the intracellular resistance of the body or of the part of the body of the individual.

12. Process for measuring the bioelectric impedance of the body or of a part of the body of an individual, characterized in that a rectangular voltage signal (11) is applied between two excitation electrodes (20, 22) connected to the individual, the voltage between two measurement electrodes (24, 26) equally connected to the individual is measured at at least two different predetermined moments permitting a direct determination of the equivalent resistance $R_{eq}$ at these two moments of the body or of the part of the body of the individual traversed by a variable electrical signal generated by the voltage signal and to deduce therefrom the extracellular resistance $R_e$ and the intracellular resistance $R_i$ of the body or of the part of the body and that the body composition of the individual is determined by utilizing the measured values and a calculation unit (14).

13. Process for measuring according to claim 12, characterized in that a first voltage measurement is effectuated, at the end of a plateau (32) of said voltage signal (11), in order to determine the equivalent resistance $R_{eq}$ equal to the extracellular resistance $R_e$, as well as a second voltage measurement, at the end of a rising edge (31) of said voltage signal (11) to determine the equivalent resistance $R_{eq}$ equal to $R_e$ in parallel with $R_i$ and to determine, on the basis of the first voltage measurement, the intracellular resistance $R_i$ of the body or of the measured part of the body of the individual traversed by a variable electrical signal generated by the voltage signal.

14. Apparatus according to claim 1, wherein the rectangular voltage signal (11) is applied at the terminals of two excitation electrodes, and said apparatus further comprises: means permitting voltage measurements $V_b$ and $V_c$ to be effectuated at the terminals of measuring electrodes and voltage measurements $V_r$ and $V_d$ to be effectuated at the terminals of a calibrated reference resistance $R_r$; and means for calculating an equivalent resistance $R_{eq}$ of the body or of the measured part of the body according to the equation:

$$R_{eq} = R_r \cdot (V_b - V_c)/(V_d - V_r).$$

\* \* \* \* \*